US010078047B2

(12) United States Patent
Nesa et al.

(10) Patent No.: US 10,078,047 B2
(45) Date of Patent: Sep. 18, 2018

(54) MEASURING VESSEL FOR SPECTROMETRY MEASUREMENT APPARATUS

(71) Applicant: OLYTHE, Aix-en-provence (FR)

(72) Inventors: Guillaume Nesa, Aix-en-Provence (FR); Etienne Flesch, Andresy (FR)

(73) Assignee: OLYTHE, Aix-en-provence (FR)

( * ) Notice: Subject to any disclaimer, the term of this patent is extended or adjusted under 35 U.S.C. 154(b) by 0 days.

(21) Appl. No.: 15/491,119

(22) Filed: Apr. 19, 2017

(65) Prior Publication Data

US 2017/0219480 A1 Aug. 3, 2017

Related U.S. Application Data

(63) Continuation of application No. 15/023,167, filed as application No. PCT/FR2014/052320 on Sep. 18, 2014, now abandoned.

(30) Foreign Application Priority Data

Sep. 18, 2013 (FR) ...................................... 13 58974

(51) Int. Cl.
*G01N 21/05* (2006.01)
*G01N 33/497* (2006.01)
*G01N 33/98* (2006.01)
*G01N 21/3504* (2014.01)
*G01N 21/03* (2006.01)

(52) U.S. Cl.
CPC ......... *G01N 21/05* (2013.01); *G01N 21/0303* (2013.01); *G01N 21/3504* (2013.01); *G01N 33/497* (2013.01); *G01N 33/4972* (2013.01); *G01N 33/98* (2013.01); *G01N 2021/0307* (2013.01); *G01N 2021/052* (2013.01); *G01N 2201/068* (2013.01)

(58) Field of Classification Search
CPC ...................................................... G01N 21/05
See application file for complete search history.

(56) References Cited

U.S. PATENT DOCUMENTS

| 4,427,179 | A | * | 1/1984 | Price | ........................ | G01C 9/00 251/88 |
| 2005/0195392 | A1 | * | 9/2005 | Uchimura | ............... | G01N 21/05 356/246 |
| 2009/0103852 | A1 | * | 4/2009 | Hamamoto | ............ | A61B 5/097 385/12 |

FOREIGN PATENT DOCUMENTS

| CA | 2499865 | * | 3/2005 |
| CA | 2499865 | C | 7/2012 |

(Continued)

OTHER PUBLICATIONS

International Search Report issued in corresponding PCT/FR2014/052320 dated Jan. 5, 2015; 6pgs.

*Primary Examiner* — Yara B Green
(74) *Attorney, Agent, or Firm* — Maier & Maier, PLLC

(57) ABSTRACT

A measuring vessel in which a gas to be analyzed by spectrometry is intended to flow, the vessel being in the form of a hollow tube provided with a reflective material forming an optical-reflection layer, including a hollow tube is produced from a non-metallic material, and a removable supple optical article is applied against the internal surface of the hollow tube, the article including a supple flexible support, one face of the support being covered with a reflective metal material, the article being inserted in the tube so that the reflective metal material forms the optical-reflection layer.

22 Claims, 2 Drawing Sheets

(56) References Cited

FOREIGN PATENT DOCUMENTS

| | | | |
|---|---|---|---|
| CN | 201282572 | * | 7/2009 |
| CN | 201282572 Y | | 7/2009 |
| DE | 3942325 A1 | | 6/1991 |
| EP | 1306661 A1 | | 5/2003 |
| FR | 2941530 A1 | | 7/2010 |
| GB | 2392976 A | | 3/2004 |
| JP | 2012177690 A | | 9/2012 |

* cited by examiner

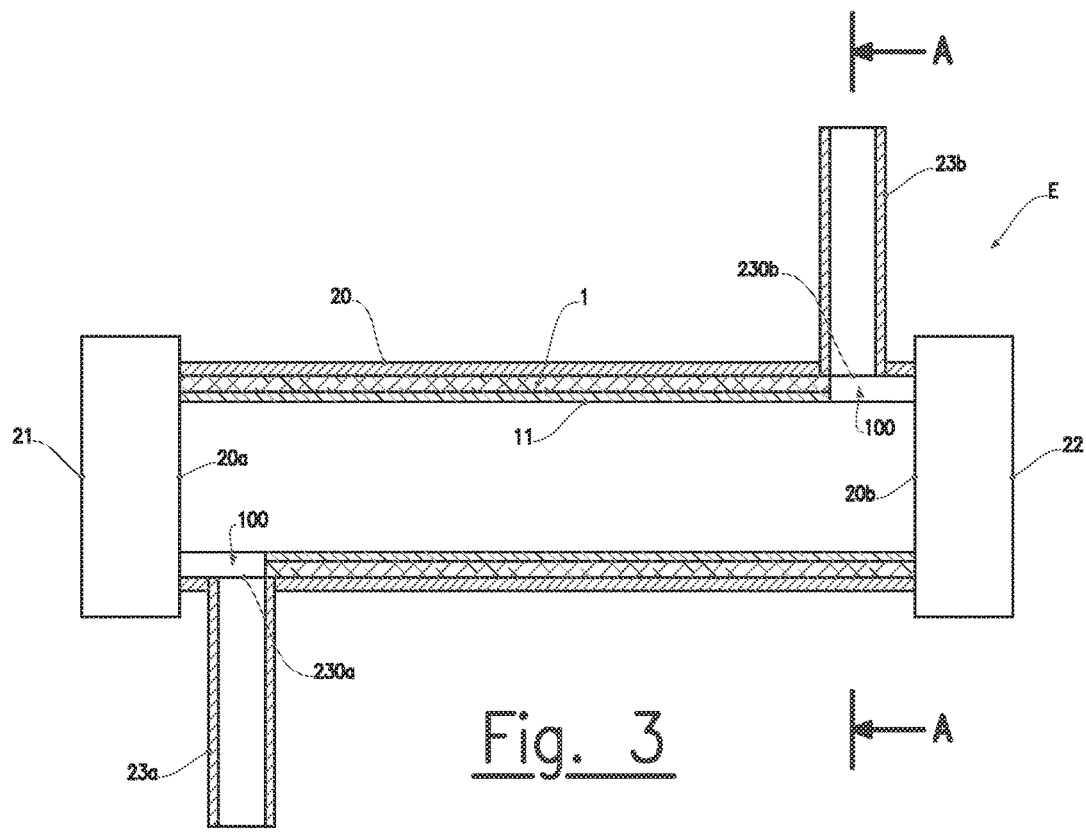
Fig. 3
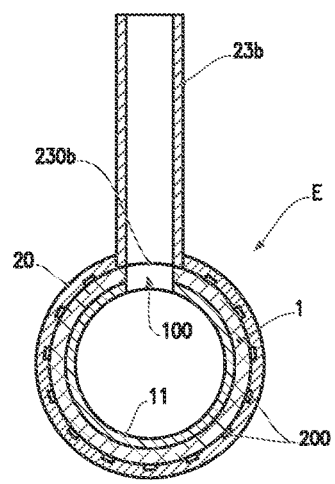
Fig. 4 (A-A)

MEASURING VESSEL FOR SPECTROMETRY MEASUREMENT APPARATUS

TECHNICAL FIELD OF THE INVENTION

One subject matter of the invention is a measuring vessel for a spectrometry measurement apparatus. Another subject matter is a spectrometry measurement apparatus integrating such a vessel. Yet another subject matter is a breathalyzer for measuring or detecting a partial gas level exhaled by a breath fluid and integrating this measuring vessel. Another subject matter thereof is a method for manufacturing a measuring vessel in which a gas to be analyzed by spectrometry is intended to flow. Finally, its subject matter is a method for producing an electromagnetic barrier in a measuring vessel.

The invention relates to the technical field of elements constituting spectrometry measurement apparatus, and more particularly elements constituting measuring vessels. It also concerns the technical field of portable electronic devices, such as breathalyzers for example, for measuring or detecting a partial gas level exhaled by a breath fluid.

PRIOR ART

A breathalyzer comprising a device emitting infrared radiation, an infrared receiver and a measuring vessel in which the breath fluid for which a partial gas level is to be measured or detected flows is known through the patent document FR 2.941.530 (SERFS ENVIRONMENT), hereinafter "SERFS document". The measuring vessel is in the form of a metal hollow tube, the internal surface of which is provided with a reflective material forming an optical-reflection layer.

In this type of apparatus, the metal tube fulfills a role of electromagnetic barrier that, in the measuring vessel, reduces any external electromagnetic fields (electrical or radio-frequency interference, electromagnetic waves, etc.).

In practice, the metal tube of the SERFS document is relatively heavy. Furthermore, its internal surface requires a specific surface treatment in order to form the optical-reflection layer. This treatment is generally complex to carry out and, in any event, is expensive.

A measuring vessel comprising a hollow tube similar to the tube of the SERFS document, and which has the same type of drawbacks, is also known through the patent document EP 1.306.661 (AGILENT TECHNOLOGIES), The invention aims to remedy this state of affairs. In particular, one objective of the invention is to propose an alternative solution for reducing the effects of electromagnetic fields external to the inside of the measuring vessel, this solution having to lead to a vessel which is lighter, less expensive and easier to manufacture than the one described in the SERFS document, while keeping the same optical quality.

Another objective of the invention is to propose a measuring vessel that can be adapted to any type of spectrometry measurement apparatus.

DISCLOSURE OF THE INVENTION

The solution proposed by the invention is a measuring vessel in which a gas to be analyzed by spectrometry is intended to flow. It is in the form of a hollow tube provided with a reflective material forming an optical-reflection layer. This vessel is remarkable in that:
the hollow tube is produced from a non-metallic material,
a removable supple optical article is applied against the internal surface of the hollow tube, said article comprising a supple flexible support, one face of said support being covered with a reflective metal material, said article being inserted in said tube so that said reflective metal material forms the optical-reflection layer.

It is now the reflective metal material of the supple optical article that fulfills the role of electromagnetic barrier rather than the tube. The latter can therefore be produced from a non-metallic, lightweight and inexpensive material and its internal surface does not require any particular surface treatment unlike the one described in the SERFS document. Furthermore, the design of the measuring vessel is simple since the optical article can be inserted in the hollow tube easily and quickly.

Other advantageous features of the measuring vessel that is the subject matter of the invention are listed below, each of these features being able to be considered alone or in combination with the remarkable features defined above:

The hollow tube preferentially has length of less than or equal to 100 mm, the optical article having a length corresponding to that of said tube.

The internal surface of the hollow tube advantageously comprises elements in relief, the optical article being in contact with the internal surfaces of said tube only at these elements in relief.

The supple flexible support is advantageously produced from a material chosen from the following group: polyimide, polyepoxide, polyester, epoxy resin reinforced with glass fiber, aluminum substrate.

The supple flexible support may have a thickness of between 1 μm and 250 μm.

The reflective material forming the optical-reflection layer is advantageously chosen from the following group: gold, cobalt, silver, nickel, copper, aluminum, chromium, zinc.

A layer may be disposed between the reflective metal material and the face of the supple flexible support, the material of this layer being able to be chosen from the following group: copper, aluminum, silver, polyethylene.

Another aspect of the invention relates to a spectrometry measurement apparatus comprising a measuring vessel in which a gas to be analyzed by spectrometry is intended to flow, the vessel being in the form of a hollow tube provided with a reflective material forming an optical-reflection layer, said vessel being in accordance with the above features.

Yet another aspect of the invention relates to a breathalyzer for measuring the partial gas level exhaled by a breath fluid, said breathalyzer comprising a device emitting infrared radiation, an infrared receiver and a measuring vessel in which the breath fluid flows, the measuring vessel being in the form of a hollow tube provided with a reflective material forming an optical-reflection layer. This breathalyzer is remarkable in that:
the hollow tube is produced from a non-metallic material,
a removable supple optical article is applied against the internal surface of the hollow tube, said article comprising a supple flexible support, one face of said support being covered with a reflective metal material, said article being positioned in said tube so that said reflective metal material forms the optical-reflection layer.

An additional aspect of the invention relates to a method for manufacturing a measuring vessel in which a gas to be analyzed by spectrometry is intended to flow, the vessel being in the form of a hollow tube provided with a reflective material forming an optical-reflection layer. According to the invention, this method consists of:

i) producing the hollow tube from a non-metallic material, ii) applying against the internal surface of the hollow tube: a removable supple optical article, said article comprising a supple flexible support, one face of said support being covered with a reflective metal material, said article being positioned in said tube so that said reflective metal material of said article forms the optical-reflection layer. This step may consist of: rolling or bending the optical article; then inserting the optical article thus rolled or bent in the hollow tube so that the reflective metal material of said article forms the optical reflection layer.

A subsidiary aspect of the invention relates to a method for producing an electromagnetic barrier in a measuring vessel in which a gas to be analyzed by spectrometry is intended to flow, the vessel being in the form of a hollow tube provided with a reflective material forming an optical-reflection layer, said tube being produced from a non-metallic material. The method consists of applying against the internal surface of the hollow tube: a removable supple optical article, said article comprising a supple flexible support, one face of said support being covered with a reflective metal material, said article being positioned in said tube so that the reflective metal material forms the optical-reflection layer and forms an electromagnetic barrier between the inside of the vessel and the internal surface of said tube.

DESCRIPTION OF THE FIGURES

Other advantages and features of the invention will emerge more clearly from a reading of the description of a preferred embodiment that follows, with reference to the accompanying drawings, produced by way of indicative and non-limitative examples, and in which:

FIG. 3 is a schematic view in longitudinal section of a breathalyzer according to the invention, FIG. 4 is a view in cross section along A-A of the breathalyzer of FIG. 3.

PREFERRED EMBODIMENTS OF THE INVENTION

The measuring vessel that is the subject matter of the invention is particularly, but not exclusively, intended to be used in a spectrometry measurement apparatus. It is in particular designed to be integrated in a breathalyzer, but may also be integrated in any other apparatus that measures a parameter (concentration of alcohol, CO, $CO_2$, $H_2O$, etc.) in a breath fluid or in any other fluid (for example a vapor or an exhaust gas).

For reasons of clarity and concision, the remainder of the description refers only to a breathalyzer, without this being able to be considered to be a limitation to the protection sought. "Breathalyzer" means, within the meaning of the present invention, any apparatus (including ethyl testing equipment) for measuring or detecting a partial gas level exhaled by a breath fluid, and in particular measuring the concentration of alcohol in the expired air and/or detecting an alcohol concentration threshold in the expired air.

Figure 1:
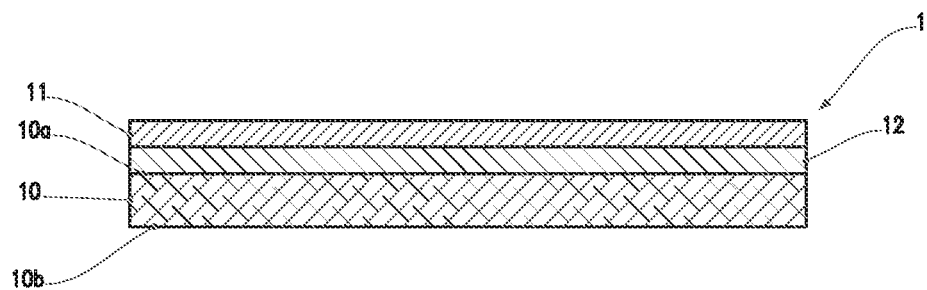
FIG. 1 is a schematic view in cross section of an optical article according to the invention.

FIG. 1 illustrates a supple optical article used to form the measuring vessel. This article 1 comprises a supple flexible support 10 consisting of a thin film having a thickness of between 1 μm and 250 μm, preferentially approximately 25 μm. A good suppleness/strength ratio is obtained with these thickness values. Its length and width are dependent on the dimensions of the measuring vessel in which it is integrated. The support 10 is advantageously produced from a material chosen from the following group: polyimide (e.g.: Kapton®), polyepoxide, polyester, epoxy resin reinforced with glass fiber, aluminum substrate (e.g.: COOL-CLAD® support marketed by the company AI TECHNOLOGY). Any other material generally used for manufacturing supple printed circuits may however be envisaged. The support 10 may be obtained by molding, extrusion, lamination, etc.

The support 10 comprises a top face 10a and a bottom face 10b that are opposite each other. In the accompanying FIG. 1, the top face 10a is covered with a reflective metal material 11 in order to form an optical-reflection layer on which the infrared radiation will rebound. Provision can however be made for the reflective metal material 11 to be deposited on the bottom face 10b. So that the reflection layer is a reflective as possible and so as to limit energy losses in the emitted radiation, the reflective metal material 11 is preferentially chosen from the following group: gold, cobalt, silver, nickel, copper, aluminum, chromium, zinc.

The reflective material 11 has a thickness of between 0.01 μm and 500 μm. It may be deposited by adhesive bonding, electrochemical deposition, electrolytic deposition, printing, screen printing, vacuum metallization, heating, or by any other fine-layer adhesion method.

For the purpose of ensuring good holding in position of the reflective material 11 on the top face 10a of the support 10, an attachment layer 12 may first be deposited on this face. This layer 12 consists for example of a layer of copper, aluminum, silver or polyethylene, the thickness of which is for example between 0.1 μm and 500 μm, deposited by a fine-layer adhesion method of the type mentioned in the previous paragraph. The layer 12 is not essential and may in particular be avoided in the case where the reflective material 11 is for example deposited by electrolytic deposition.

The integration of the article 1 in the measuring vessel of a portable breathalyzer will now be detailed with reference to FIGS. 3 and 4. This breathalyzer E is of the type described in the aforementioned SERFS document. The measuring vessel is in the form of a hollow tube 20. The latter typically has a circular cross section but may have a square, rectangular, oval, etc. cross section. The tube 20 may be produced from a non-metallic material, for example plastics material (e.g. PVC, ABS), carbon composite material, etc. It may be obtained by molding, extrusion or any other method suitable for a person skilled in the art. Its internal surface does not require any particular surface treatment, unlike the one described in the SERFS document.

According to a preferred embodiment, the length of the tube 20 is between 5 mm and 200 mm, preferentially less than or equal to 100 mm, the invention making it possible to use a shorter measuring vessel than that of the SERFS document. Its inside diameter is less than 15 mm, for example between 4 mm and 15 mm. And its thickness is less than 5 mm, for example between 1 mm and 5 mm.

One end 20a of the tube 20 is provided with a device 21 for emitting infrared radiation, advantageously in wavelengths of between 1 μm and 12 μm. The other end 20b is provided with an infrared receiver 22. The emitter 21 and the infrared receiver 22 are of the type known to persons skilled in the art. The breath fluid flows in the measuring vessel between the two ends 20a, 20b of the tube 20. More particularly, the fluid enters the tube 20 by means of an inlet nozzle 23a (in which the user blows) installed at the end 20a, and emerges from said tube by means of an outlet nozzle 23b installed at the opposite end 23b The two nozzles 23a and 23b may be situated on the same side of the tube 20, or on the contrary on two opposite sides (FIG. 3). A pumping system may be associated with the nozzles 23a and 23b in order to ensure flow of the blown fluid sample.

The article 1 is inserted in the tube 20 so that the reflective metal material 11 forms the optical-reflection layer. When the tube 20 has a circular cross section, the article 1 is rolled, manually or automatically, so as to form a cylinder. In the case where the tube 20 has not a circular cross section, but a square, rectangular or other polygonal-shaped cross section, the article 1 is bent so as to form a tube having this particular cross section. The reflective metal material 11 forms the internal surface of this cylinder (or tube). This arrangement optimizes the lengths of the optical paths in the tube 20, while keeping sufficient quantity of light as far as the receiver 22. As a result the measuring vessel may be shorter than that of the breathalyzer described in the SERFS document.

The optical article 1 has a length corresponding to that of the tube 20 so that the internal surface of the latter is completely, or substantially completely, covered by said article. This is because some zones of the internal surface of the tube 20 may not be covered, in particular at the ends 20a and 20b, while keeping an acceptable measuring quality.

The article 1 thus conformed is then inserted in the tube 20, at one of the ends 20a or 20b, so that the reflective material 11 forms the optical-reflection layer against which the infrared radiation will rebound. In the configuration in FIG. 1, it is the internal face 10b of the support 10 that is in contact with the internal surface of the tube 20.

Thus positioned between the internal surface of the tube 20 and the inside of the measuring vessel, the optical article 1—and more precisely the reflective metal material 11—forms an electromagnetic barrier. All or parts of the external electromagnetic fields liable to enter inside the measuring vessel and to interfere with the infrared receiver 20—and therefore the precision of the measurement—are in fact stopped by the reflective metal material 11.

When the article 1 is formed, it has a natural tendency to unwind (or unfold) in order to regain its original flat shape. The result of this ability is that the article 1 is naturally held in position inside the tube 20 without its being necessary to provide another mechanical fixing system or one by adhesive bonding. Such a system may however be envisaged as a precautionary measure.

The internal surface of the tube 20 may comprise elements in relief 200. The later consist for example of longitudinal or radial ribs, or in any other form having hollows and protrusions on the internal surface of the tube 20. As is clear in FIG. 4, when the optical article 1 is inserted in the tube 20, it is in contact only with these elements in relief 200.

Once the article 1 is shaped and installed in the tube 20, and the measuring vessel is thus manufactured, the other components 21, 22, 23a, 23b are fitted.

Figure 2:
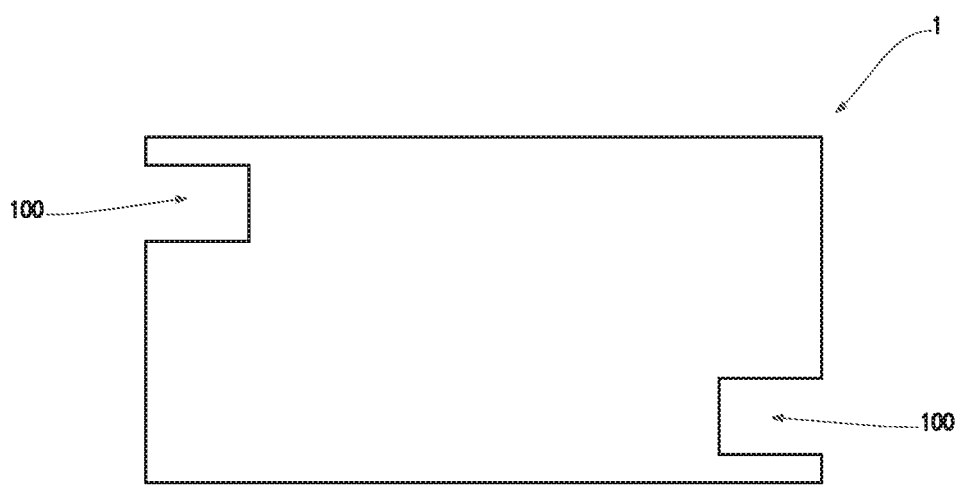
FIG. 2 is a schematic plan view of an optical article according to FIG. 1.

With regard to the nozzles 23a, 23b, it is necessary that they emerge inside the measuring vessel, despite the presence of the article 1 that covers the internal surface of the tube 20. To do this, and as will appear in FIG. 2, the article 1 comprises notches, piercings or, more generally, recesses 100, the dimensions of which are adjusted to the diameters of the nozzles 23a, 23b. These recesses 100 are situated at the lateral edges of the article 1. When the article 1 is shaped and inserted in the tube 10, the recesses 100 are placed opposite the emerging ends 230a, 230b of the nozzles 23a, 23b and leave the latter free.

The arrangement of the various elements and/or means and/or steps of the invention, in the embodiments described above, must not be understood as requiring such an arrangement in all implementations. In any event, it will be understood that various modifications may be made to these elements and/or means and/or steps without departing from the spirit and scope of the invention. In particular, the measuring vessel may be used for processing signals other than infrared signals and/or with an analysis technique other than spectrometry.

The invention claimed is:

1. A measuring vessel in which a gas to be analyzed by spectrometry is intended to flow, the vessel being in the form of a hollow tube provided with a reflective material forming an optical-reflection layer, comprising:
   the hollow tube includes an internal surface,
   the hollow tube is produced from a non-metallic material,
   a removable supple optical article is applied against the internal surface of the hollow tube, said article comprising a supple flexible support,
   the supple flexible support comprises a top face and a bottom face that are opposite each other,
   the top face of said support being covered with a reflective metal material,
   the bottom face of said support being in contact with the internal surface of the hollow tube, and
   the removable supple optical article being inserted in the hollow tube so that the reflective metal material forms the optical-reflection layer.

2. The vessel according to claim 1, in which the hollow tube has a length less than or equal to 100 mm, the optical article having a length corresponding to that of said tube.

3. The vessel according to on claim 1, in which the internal surface of the hollow tube comprises elements in relief, the optical article being in contact with the internal surface of said tube only at these elements in relief.

4. The vessel according to claim 1, in which the material forming the supple flexible support is a polyimide.

5. The vessel according to claim 1, in which the supple flexible support has a thickness of between 1 μm and 250 μm.

6. The vessel according to claim 1, in which the reflective metal material has a thickness of between 0.01 μm and 500 μm.

7. The vessel according to claim 1, in which the reflective metal material forming the optical reflection layer is gold.

8. The vessel according to claim 1, in which a layer is disposed between the reflective metal material and the top face of the supple flexible support.

9. The vessel according to claim 8, in which the material of the layer is chosen from the following group: copper, aluminum, silver, polyethylene.

10. The vessel according to claim 1, in which the non-metallic material forming the hollow tube is chosen from the following group: plastics material, carbon, composite material.

11. A breathalyzer for measuring the partial gas level exhaled by a breath fluid, said breathalyzer comprising:
    a device emitting infrared radiation, an infrared receiver and a measuring vessel in which the breath fluid flows, the measuring vessel being in the form of a hollow tube provided with a reflective material forming an optical-reflection layer, wherein that said vessel includes:
    a hollow tube comprising an internal surface,
    the hollow tube being produced from a non-metallic material, a removable supple optical article being applied against the internal surface of the hollow tube, said article comprising a supple flexible support,
the supple flexible support comprises a top face and a bottom face that are opposite each other,
the top face of said support being covered with a reflective metal material,
the bottom face of said support being in contact with the internal surface of the hollow tube, and
the removable supple optical article being inserted in the hollow tube so that the reflective metal material forms the optical-reflection layer.

12. A method for manufacturing a measuring vessel in which a gas to be analyzed by spectrometry is intended to flow, the vessel being in the form of a hollow tube provided with a reflective material forming an optical-reflection layer, characterized by the fact that the method comprising:
    i) producing the hollow tube from a non-metallic material, the hollow tube being formed with an internal surface; and
    ii) applying against the internal surface of the hollow tube: a removable supple optical article, said article comprising a supple flexible support comprising a top face and a bottom face that are opposite each other,
    iii) covering the top face of said support with a reflective metal material,
    iV) positioning said article in said tube so that:
        the bottom face of said support being in contact with the internal surface of the hollow tube,
        the reflective metal material of said article forms the optical-reflection layer.

13. The method according to claim 12, in which further comprises:
    rolling or bending the optical article; and
    inserting the optical article thus rolled or bent in the hollow tube so that the reflective metal material of said article forms the optical-reflection layer.

14. The method according to claim 12, in which further comprises:
    producing the removable supple optical article by molding.

15. The method according to claim 12, in which further comprises:
    producing the removable supple optical article by extrusion.

16. The method according to claim 12, in which further comprises:
    producing the removable supple optical article by lamination.

17. The method according to claim 12, depositing the reflecting metal material by adhesive bonding.

18. The method according to claim 12, in which further comprises:
    depositing the reflective metal material by electrochemical deposition.

19. The method according to claim 12, in which further comprises:
    depositing the reflective metal material by electrolytic deposition.

20. The method according to claim 12, in which further comprises:
    depositing the reflective metal material by printing.

21. The method according to claim 12, in which further comprises:
    depositing the reflective metal material by screen printing.

22. The method according to claim 12, in which further comprises:
    depositing the reflective metal material by vacuum metallization.

* * * * *